(12) United States Patent
von Bülow et al.

(10) Patent No.: US 8,574,199 B2
(45) Date of Patent: Nov. 5, 2013

(54) COUPLING FOR INJECTION DEVICES

(75) Inventors: Martin von Bülow, Helsingoer (DK); Lars Ulrik Nielsen, Virum (DK)

(73) Assignee: Novo Nordisk A/S, Bagsvaerd (DK)

( * ) Notice: Subject to any disclaimer, the term of this patent is extended or adjusted under 35 U.S.C. 154(b) by 288 days.

(21) Appl. No.: 12/305,729

(22) PCT Filed: Jun. 7, 2007

(86) PCT No.: PCT/EP2007/055621
§ 371 (c)(1),
(2), (4) Date: Mar. 19, 2009

(87) PCT Pub. No.: WO2008/003560
PCT Pub. Date: Jan. 10, 2008

(65) Prior Publication Data
US 2009/0254043 A1 Oct. 8, 2009

Related U.S. Application Data
(60) Provisional application No. 60/819,190, filed on Jul. 7, 2006.

(30) Foreign Application Priority Data
Jul. 3, 2006 (EP) .................................. 06116511

(51) Int. Cl.
*A61M 5/00* (2006.01)
(52) U.S. Cl.
USPC ........... 604/211; 604/110; 604/181; 604/187; 604/192; 604/193; 604/194; 604/198

(58) Field of Classification Search
USPC ......... 604/110, 181, 187, 192, 193, 194, 198, 604/211
See application file for complete search history.

(56) References Cited

U.S. PATENT DOCUMENTS 6,004,297 A * 12/1999 Steenfeldt-Jensen et al. .............................. 604/207
2003/0236502 A1 12/2003 De La Serna et al.

FOREIGN PATENT DOCUMENTS

| | | |
|---|---|---|
| CN | 1243578 A | 2/2000 |
| EP | 0897728 * | 2/1999 |
| EP | 897728 | 2/1999 |
| JP | 11-104240 A | 4/1999 |
| JP | P3270761 A | 1/2002 |
| JP | 3414760 | 4/2003 |
| JP | 2005518907 A | 6/2005 |
| JP | 2005536300 A | 12/2005 |
| WO | 9916487 | 4/1999 |
| WO | WO 99/16487 | 4/1999 |
| WO | 9938554 | 8/1999 |
| WO | 03076001 | 9/2003 |

* cited by examiner

*Primary Examiner* — Kevin C Sirmons
*Assistant Examiner* — Edelmira Bosques
(74) *Attorney, Agent, or Firm* — Wesley A. Nicolas; Marc A. Began; Reza Green

(57) ABSTRACT

The present invention concerns a prefilled injection device having a container and a dose setting mechanism encapsulated inside the housing. The housing is made from two parts which are locked together by a bayonet coupling: In addition to the bayonet coupling, the two parts are also provided with irreversible locking means locking the two parts permanently together.

11 Claims, 3 Drawing Sheets

COUPLING FOR INJECTION DEVICES

CROSS-REFERENCE TO RELATED APPLICATIONS

This application is a 35 U.S.C. §371 national stage application of International Patent Application PCT/EP2007/055621 (published as WO 2008/003560), filed Jun. 7, 2007, which claimed priority of European Patent Application 06116511.4, filed Jul. 3, 2006; this application further claims priority under 35 U.S.C. §119 of U.S. Provisional Application 60/819,190, filed Jul. 7, 2006.

THE TECHNICAL FIELD OF THE INVENTION

The invention relates to a bayonet coupling for an injection device and preferably for a bayonet coupling in combination with irreversible locking means.

DESCRIPTION OF RELATED ART

People suffering from diabetes are often treated with multiple daily injections in a regimen comprising one or two daily injections of a long acting insulin to cover the basal requirement supplemented by bolus injections of a short or rapid acting insulin to cover requirements related to meals.

Generally speaking two different types of pen systems are used for the treatment of diabetes. The first type being injection devices with a replaceable cartridge containing the insulin to be injected. Often such cartridges contain 3 ml of insulin, and when this amount has been injected a new cartridge is inserted in the same injection device which therefore often is in use for several years. Such injections devices are usually referred to durable injection devices.

An example of such durable injection device where the cartridge is connected to the injection device by way of a bayonet coupling is disclosed in e.g. WO 99/16487 and EP 897,728.

The other type being injection devices containing a predetermined and non-replaceable amount of insulin, also often 3 ml. The insulin is often contained in a cartridge embedded in the injection device. When the predetermined amount has been injected which in average takes anywhere from a few days to a month, the entire injection device is discarded and a new injection device is used for subsequent injections. Such injection devices are often referred to as disposable of prefilled injection pens.

An example of such prefilled injection pen where the parts forming the housing is irreversible clicked together is known from U.S. Pat. No. 6,004,297

When clicking the parts together the tolerances must be calculated such that the click- or snap function will always be activated i.e. the tolerances must be such that the point of no return is always reached during assembly. This however can result in some slack being introduced in the mechanical locking of the elements.

DESCRIPTION OF THE INVENTION

It is an object of the present invention to provide an irreversible mechanical locking that does not introduce slack between the parts locked together.

A bayonet coupling as the one known e.g. from WO 99/16487 has the advantage that the two elements is pressed together when the two parts are rotated relatively due to the angle of the protrusion and the bayonet thread.

Combining such bayonet coupling with an irreversible mechanical lock locking the parts together makes the solution very attractive to prefilled injection devices due to the fact that the press fitting of the two elements can reduce the slack occurring due to the injection moulding process involved in producing the various parts. The mechanical lock can be formed such that it locks into its locking position when the two elements are sufficiently pressed together by the bayonet coupling. In this way the mechanical slack can be reduced or even avoided.

The bayonet coupling is provided with a click-lock which secures the two parts when they are axially pressed together. The click-lock comprises a protrusion and a well. Both the protrusion and the well are inclined in such way that the well forms a steep edge and the protrusion forms a steep front. When the two parts are axially pressed together the inclined protrusion slides in the track until the protrusion falls into the well with the steep front of the protrusion locked behind the steep edge of the well preventing the two parts from being separated.

When the steep edge and/or the steep front are angled, the two parts of housing will be pulled tighter together when relatively rotated.

With the well having a peripheral extension greater than the width of the track, the two parts can be rotated relatively to each other once the protrusion has entered into the well.

The means irreversible locking the parts together are located separate from the bayonet coupling and comprises a longitudinal shaped elevation which is guided up a ramp and abruptly brought into a locking well. The ramp follows the peripheral extension of the injection pen such that when the two parts are rotated and the protrusion is moved into the peripheral extension of the well, the longitudinal shaped elevation is moved up the ramp until it falls over the abruptly interrupted ramp and into the locking well.

Once the longitudinal elevation is secured in the locking well, the two parts can not be rotated relatively to each other and with the protrusion located in the pheriferal extension of well it is axially secured by the raised wall forming the well so the two parts can not be separated.

Definitions

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

Further the term "injection needle" defines a piercing member adapted to penetrate the skin of a subject for the purpose of delivering or removing a liquid.

"Cartridge" is the term used to describe the container containing the insulin. Cartridges are usually made from glass but could also moulded from any suitable polymer. A cartridge or ampoule is preferably sealed at one end by a pierceable membrane which can be pierced e.g. by an injection needle. The opposite end is closed by a plunger or piston made from rubber or a suitable polymer. The plunger or piston can be slidable moved inside the cartridge. The space between the pierceable membrane and the movable plunger holds the insulin which is pressed out as the plunger decreased the volume of the space holding the insulin.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the injection device carrying the injection needle whereas the term "proximal end" is meant to refer to the opposite end pointing away from the injection needle.

Figure 1:
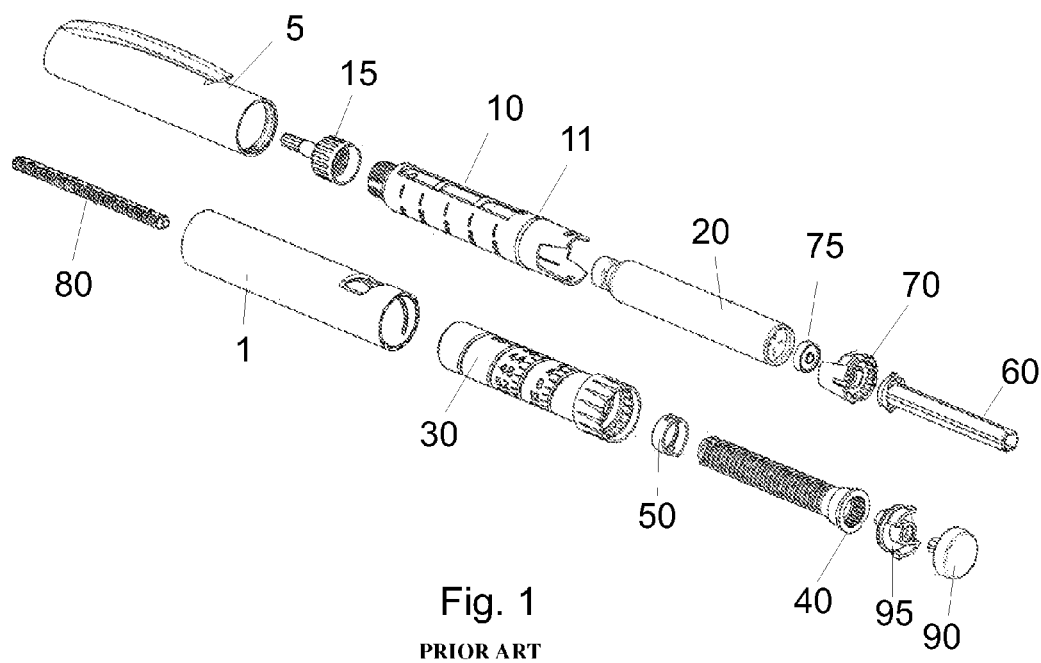
FIG. 1 Shows an exploded view of a prior art injection pen.
Figure 2:
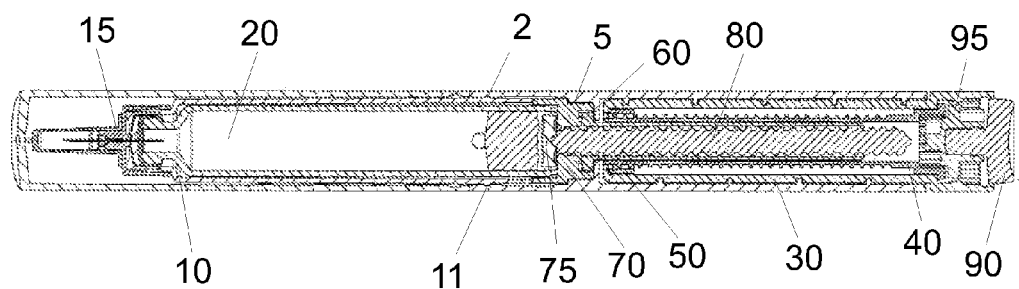
FIG. 2 Shows a cross section of the prior art injection pen of FIG. 1.

FIGS. 1 and 2 discloses the injection device market by the company Novo Nordisk A/S under the trade name FlexPen® and disclosed in U.S. Pat. No. 6,004,297 and U.S. Pat. No. 6,235,004. The injection device comprises a dose setting and injection mechanism and a container 20 in the form of a glass cartridge containing the liquid medicament. The dose setting and injection mechanism and the container 20 are permanently embedded in a housing. The housing comprises two parts; a first proximal part 1 encapsulating the dose setting and injection mechanism and a second distal part 10 referred to as the cartridge-holder surrounding the container 20.

The first part 1 and the second part 10 are preferably clicked together during the manufacture of the injection device in a way making it almost impossible for the average user to separate the two parts 1, 10. This is done by engagement of a rim 11 on the second part 10 with a groove 2 located on the inside surface of the first part 1. The cartridge 20 containing the liquid drug is in this way permanently embedded in the connection between the first part 1 and the second part 10.

The dose setting and injection mechanism comprises, starting from the housing; a scale drum 30, a connector tube 40, a piston rod guide 60 and a threaded piston rod 80. The threaded piston rod 80 is screwed forward in a nut member 70 pushing a piston foot 75 forward into the container 20. The proximal end of the housing is closed by an injection button 90 secured in a clicker element 95. An injection needle 15 is secured at the distal end of the housing. The distal end of the injection pen is preferably covered by a cap 5.

Further an End-of-Dose mechanism is provided in the form of a guided End-of-Content ring 50. This mechanism is described in details in EP 1.250.167.

Figure 3:
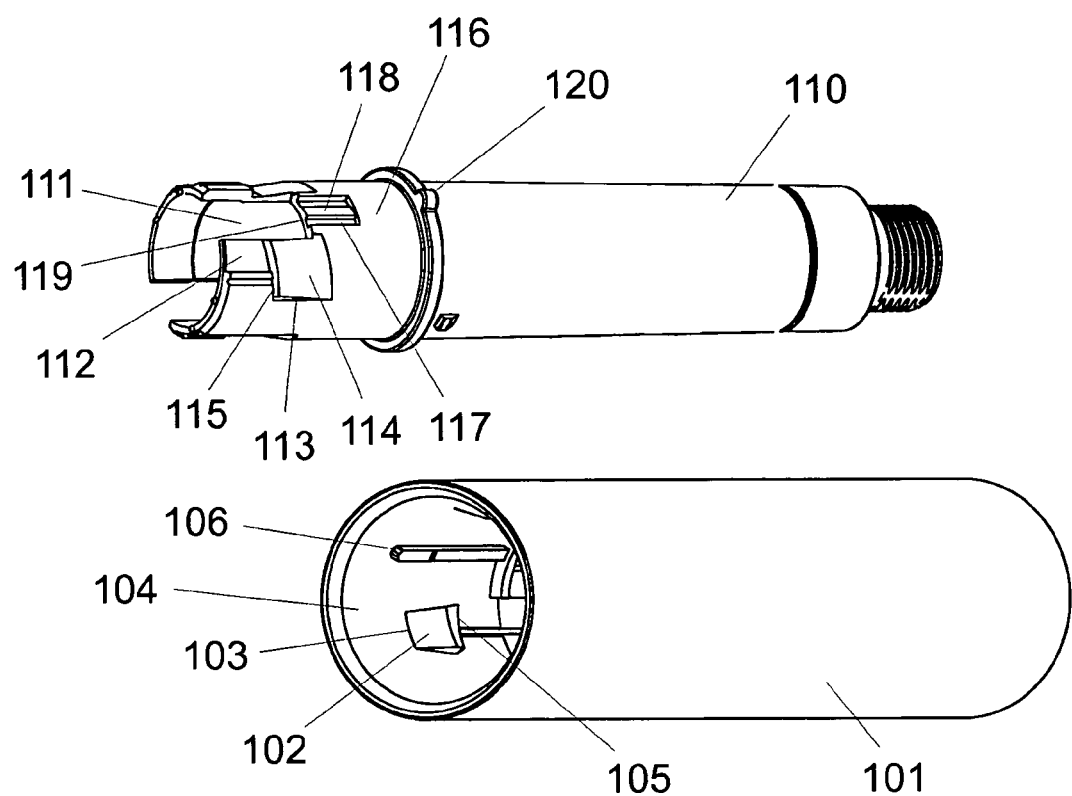
FIG. 3 Shows an exploded view of the combined bayonet coupling and permanent lock.

FIG. 3 discloses an alternative way of securing the first part 101 and the second part 110.

The first part 101 is provided with a number of protrusions 102 which has an inclined shape. At the distal end of the protrusion 102, the top surface 103 is in level with the inside surface 104 of the first part 101 whereas the protrusion 102 slopes inwardly in the proximal direction to form a ramp. The proximal end of the protrusion 102 forms a steep front 105 which is angled a few degrees relatively to the perpendicular direction of the injection device.

Figure 4:
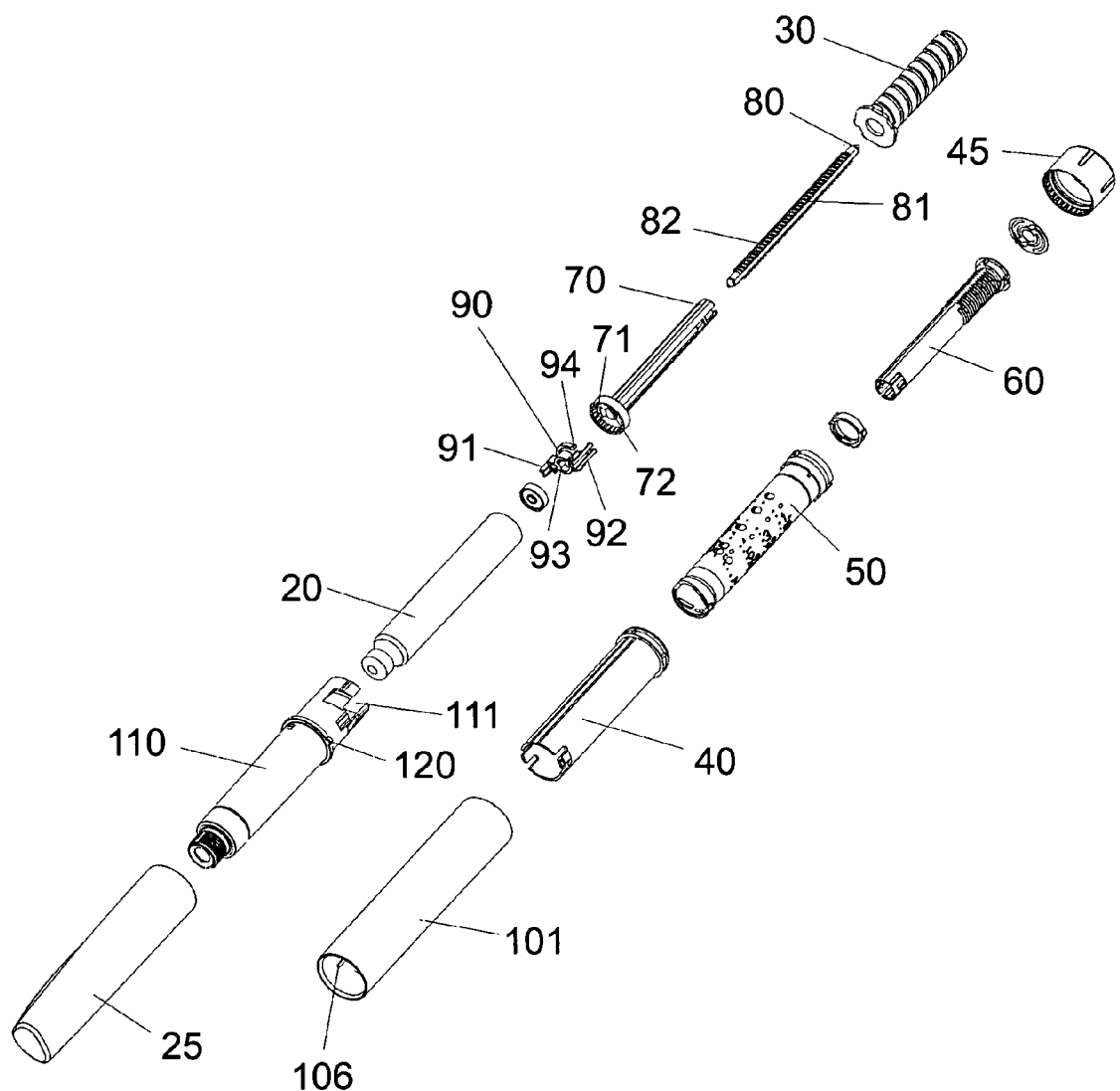
FIG. 4 Shows an exploded view of an alternative injection pen.

The second part 110 is provided with a number of open tracks 111 into which open tracks 111 the legs 91, 92 of the nut member 90 is guided during assembly of the injection device as indicated in FIG. 4. In addition to these open tracks 111 for securing the nut member 90, a second number of tracks 112 are also provided. When the legs 91, 92 of the nut member 90 are located in the open tracks 111, these legs 91, 92 also form part of the bottom surface of the second tracks 112. The second tracks 112 leads into a well 113 which has a steep edge 115 at the proximal side and an inclined bottom surface 114 leading up to the level of the inner surface 116 of the second part 110. The well 113 preferably has the same shape as the protrusion 102 such that the protrusion 102 can fit into the well 113 when the injection device is assembled.

The steep front 115 is angled a few degrees relatively to the perpendicular direction of the injection device.

When the first part 101 and the second part 110 are pushed together the protrusion 102 will slide in the second track 112 and be guided into the well 113. The steep front 105 will drop over the steep edge 115 whereby the first part 101 and second part 110 clicks together. The well 113 has a sideward size that is greater than the sideward extension of the protrusion 102 such that once the protrusion 102 has entered the well 113 the first 101 and the second part 110 can be rotated relatively to each other. By doing so, the protrusion 102 is moved from the second track 112 and sideward into the well 113 whereby the protrusion 102 is axially locked behind the part of the inner surface 116 rising above the second track 112.

Once the steep front 105 is locked by the steep edge 115, the first part 101 and the second part 110 can only be pulled apart by using excessive force.

The steep front 105 and the steep edge 115 together forms a click lock 105, 115 locking the two parts 101, 110 together during assembly. However, to entirely prevent a user from disassembling the injection pen and gain access to the cartridge 20 containing the liquid drug an irreversible lock 106, 117 is provided in addition to the click lock 105, 115.

The permanent lock 106, 117 between the first part 101 and the second part 110 of the housing is formed by a longitudinal elevation 106 on the first part 101 engaging a locking well 117 located at the proximal end of the second part 110 of the housing.

The locking well 117 is formed at the end of an abruptly interrupted ramp 118. The ramp 118 starts from a low level and slopes upwardly until it is abruptly interrupted by a steep locking edge 119 forming the locking well 117. The sloping of the ramp 118 follows the periphery of the second part 110.

In order to lock the first part 101 and the second part 110, the protrusion 102 is guided through the first track 112 and into the well 113. Once the protrusion 102 is clicked into the well 113, the longitudinal elevation 106 has moved over the low level of the ramp 118. When the first part 101 and the second part 110 is rotated relatively the protrusion 102 moves sideward in the well 113 as the longitudinal elevation 106 is forced up the ramp 118 until it falls down the steep locking edge 119 forming the locking well 117. With the longitudinal elevation 106 located in the locking well 117, the first part 101 and the second part 110 can not be rotated relatively to each other and with the protrusion 102 anchored in the well 113, the two parts 101, 110 can not be separated and is thus permanently and irreversible fixed to each other.

Since the steep front 105 and the steep edge 115 has an angle a few degrees from the perpendicular direction of the injection device, the first 101 and the second part 110 is pulled tight to each other as the two parts 101, 110 are rotated relatively as the protrusion 102 rotates sideward in the well 113 along the periphery of the injection device.

The injection pen disclosed in FIG. 4 is very similar to the injection pen described in PCT/EP2006/050800.

The injection pen comprises a housing made up of a first part 101 and a second part 110, the second part 110 being covered by a cap 25 when not in use. The cap 25 can be provided with means assisting the user in handling the injection needle e.g. by having an aperture which can secure the inner cap of the injection needle while performing the injection. Either part of the housing could on the external surface be provided with a knob 120 preventing the injection pen from rolling on a surface. A cartridge 20 containing the drug is located in the second part 110 and a thread tower 30 is secured to the first part 101.

Further the dose setting and injection mechanism comprises, starting from the housing; a shield 40, a scale drum 50, a connector pipe 60, a piston rod guide 70 and a piston rod 80.

The shield 40 is connected to the push button 45, which could be provided with a soft grip texture on the outer surface. A nut member 90 having legs 91, 92 is secured to the second part 110 of the housing by the legs 91, 92 engaging the open track 111 of the second part 110. The nut member 90 further has a keyed opening 93 matching the keyed shape 81 of the piston rod 80 such that the piston rod 80 can slide axially in the nut member 90. The nut member 90 further has a number of ratchet arms 94 engaging a toothed ring 71 provided in the piston rod guide 70 such that the piston rod guide 70 is only rotatable in one direction relatively to nut member 90.

The piston rod guide 70 is provided with an internal thread 72 engaging the external thread 81 on the piston rod 80 such that when the piston rod guide 70 is rotated the piston rod 80 is moved forward in the nut member 90. The ratchet engagement 93, 71 being such that the piston rod 80 can only be moved forward i.e. in the distal direction.

The working of the injection pen is described in PCT/EP2006/050800 in relation to FIGS. 8 and 9.

Some preferred embodiments have been shown in the foregoing, but it should be stressed that the invention is not limited to these, but may be embodied in other ways within the subject matter defined in the following claims. The figures e.g. discloses the injection device of the present invention in the form of an oblong pen-shaped object, however, this particular shape is in no way limiting for the present invention as defined in the claims.

The invention claimed is:

1. An apparatus for performing medical injections comprising;
a housing having a longitudinal axis,
a container containing a liquid medicament,
a dose setting and injection mechanism,
wherein the container and the dose setting mechanism are encapsulated inside the housing, which comprises a first part and a second part locked together by a bayonet coupling and an irreversible locking element that is separate from the bayonet coupling and permanently locks the first part and the second part together, the irreversible locking element including a longitudinal elevation substantially parallel to the longitudinal axis of the housing.

2. An apparatus for performing medical injections according to claim 1, wherein one of the first part or second part comprises at least one track that is approximately parallel to the longitudinal axis of the housing and terminates in a well, and wherein the other one of the first part or second part comprises a protrusion.

3. An apparatus for performing medical injections according to claim 2, wherein each one of the well and the protrusion is inclined along the longitudinal axis of the housing.

4. An apparatus for performing medical injections according to claim 3, wherein the inclined well forms a steep edge and the inclined protrusion forms a steep front.

5. An apparatus for performing medical injections according to claim 4, wherein the steep edge and/or the steep front is angled with respect to a plane perpendicular to the longitudinal axis of the housing.

6. An apparatus for performing medical injections according to claim 5, wherein the well has a peripheral extension greater than the width of the protrusion.

7. An apparatus for performing medical injections according to claim 1, wherein the longitudinal elevation of the irreversible locking element is arranged on one of the first part or the second part, and the irreversible locking means further includes a ramp having an abrupt interruption along the longitudinal axis of the housing, the ramp being arranged on the other of the first part or the second part.

8. An apparatus for performing medical injections according to claim 7, wherein the abrupt interruption of the ramp and a steep end surface of the ramp together define a locking well that engages the longitudinal elevation and irreversible locks the first part and the second part together.

9. An apparatus for performing medical injections according to claim 1, wherein the bayonet coupling includes a protrusion formed in an inner surface of the first part and a corresponding track formed on an outer surface of the second part, the longitudinal elevation of the irreversible locking element being arranged on the inner surface of the first part, the irreversible locking element further comprising a ramp arranged on the outer surface of the second part, the ramp having an abrupt interruption along the longitudinal axis of the housing that engages the longitudinal elevation.

10. An apparatus for performing medical injections according to claim 9, wherein the track of the bayonet coupling terminates in a well having a steep edge that engages a terminal end of the protrusion of the bayonet coupling.

11. An apparatus for performing medical injections according to claim 10, wherein the protrusion and the well of the bayonet coupling are each inclined along the longitudinal axis of the housing.

\* \* \* \* \*